United States Patent [19]

Ishizumi et al.

[11] Patent Number: 4,545,936
[45] Date of Patent: Oct. 8, 1985

[54] NOVEL AMINONAPHTHACENE DERIVATIVES AND PROCESS FOR PREPARATION THEREOF

[75] Inventors: Kikuo Ishizumi, Toyonaka; Michihisa Muramatsu, Osaka; Hiromi Sato, Toyonaka; Norihiko Tanno, Ibaraki; Noboru Yoshida, Osaka, all of Japan

[73] Assignee: Sumitomo Chemical Company, Limited, Osaka, Japan

[21] Appl. No.: 607,268

[22] Filed: May 4, 1984

Related U.S. Application Data

[63] Continuation-in-part of Ser. No. 490,759, May 2, 1983, abandoned.

[30] Foreign Application Priority Data

May 7, 1982 [JP] Japan .................................. 57-76835

[51] Int. Cl.$^4$ ...................... C07C 15/24; C07C 50/22; C07C 50/36
[52] U.S. Cl. .................................. 260/377; 260/351.1; 260/351.5; 260/365
[58] Field of Search ...................... 260/377, 365, 351.1, 260/351.5

[56] References Cited

PUBLICATIONS

"The Journal of Medicinal Chemistry", vol. 22, No. 8, pp. 922–926 (1979).
"The Journal of Medicinal Chemistry", vol. 72, No. 11, pp. 1425–1428 (1979).

*Primary Examiner*—Glennon H. Hollrah
*Assistant Examiner*—Raymond Covington
*Attorney, Agent, or Firm*—Birch, Stewart, Kolasch & Birch

[57] ABSTRACT

An aminonaphthacene derivative of the formula:

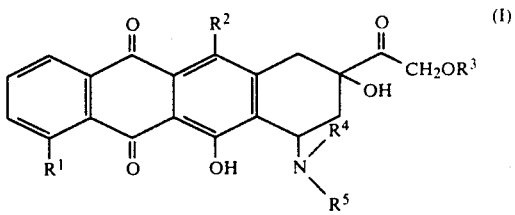

wherein $R^1$ is a hydrogen atom, a hydroxyl group or a lower alkoxy group, $R^2$ is a hydrogen atom or a hydroxyl group, $R^3$ is a hydrogen atom or a lower alkanoyl group and $R^4$ and $R^5$ are, same or different, each a hydrogen atom, a lower alkyl group, a lower hydroxyalkyl group or a group of the formula:

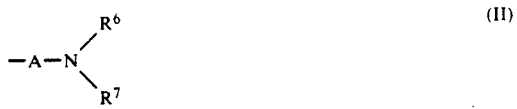

wherein A is an alkylene group which may have one or more lower alkyl substituent(s) and $R^6$ and $R^7$ are, same or different, each a hydrogen atom, a lower alkyl group, a lower hydroxyalkyl group or a lower aminoalkyl group, and an acid addition salt thereof, which is useful as anti-tumor agent.

4 Claims, No Drawings

NOVEL AMINONAPHTHACENE DERIVATIVES AND PROCESS FOR PREPARATION THEREOF

This is a continuation-in-part application of our copending application Ser. No. 490,759 filed on May 2, 1983 now abandoned.

The present invention relates to novel aminonaphthacene derivatives and a process for preparation thereof. More particularly, it relates to 7-amino-5,7,8,9,10,12-hexahydronaphthacene derivatives of the formula:

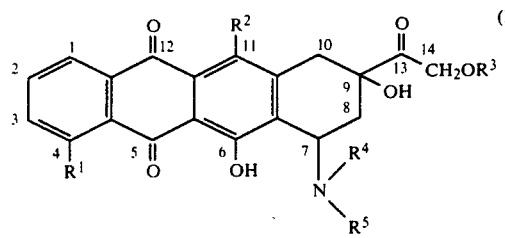

wherein $R^1$ is a hydrogen atom, a hydroxyl group or a lower alkoxy group, $R^2$ is a hydrogen atom or a hydroxyl group, $R^3$ is a hydrogen atom or a lower alkanoyl group and $R^4$ and $R^5$ are, same or different, each a hydrogen atom, a lower alkyl group, a lower hydroxyalkyl group or a group of the formula:

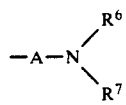

wherein A is an alkylene group which may have one or more lower alkyl substituent(s) and $R^6$ and $R^7$ are, same or different, each a hydrogen atom, a lower alkyl group, a lower hydroxyalkyl group or a lower aminoalkyl group.

In the above significances, the term "lower alkyl" is intended to mean straight or branched alkyl having 1 to 4 carbon atoms; specific examples are methyl, ethyl, n-propyl, isopropyl, n-butyl, isobutyl, t-butyl, etc. Likewise, the term "lower alkoxy" means those having 1 to 4 carbon atoms; specific examples are methoxy, ethoxy, n-propoxy, isopropoxy, n-butoxy, isobutoxy, t-butoxy, etc. The term "lower alkanoyl" denotes alkanoyl having 1 to 5 carbon atoms and may be exemplified by formyl, acetyl, propionyl, butyryl, isobutyryl, valeryl, isovaleryl, etc. The term "alkylene" denotes a straight alkylene chain having 2 to 8 carbon atoms and more specifically represents a group of the formula: —(CH$_2$)$_m$— wherein m is 2 to 8. The alkylene chain may be substituted with one or more $C_1$-$C_4$ lower alkyl. The terms "lower hydroxyalkyl" and "lower aminoalkyl" denote respectively $C_1$-$C_4$ alkyl substituted with hydroxyl and $C_1$-$C_4$ alkyl substituted with amino, the substituent being not present at the carbon atom adjacent to the nitrogen atom in the formula (I) or (II). The term "halogen" means fluorine, chlorine, bromine or iodine.

The compound represented by the formula (I) can be prepared by the process as set forth below.

A compound of the formula:

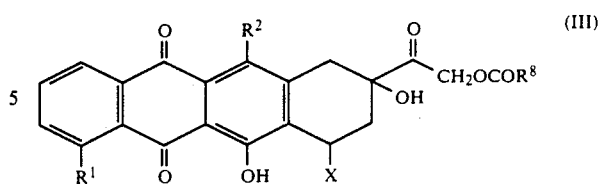

wherein $R^8$ is a lower alkyl group and X is a halogen atom and $R^1$ and $R^2$ are each as defined above is reacted with a compound of the formula:

wherein $R^4$ and $R^5$ are each as defined above to produce a compound of the formula:

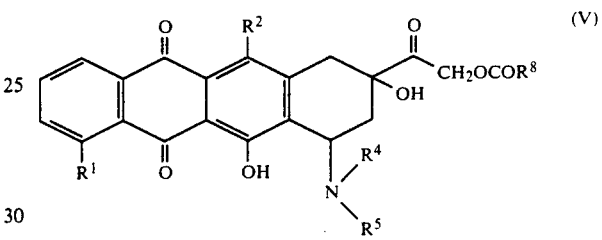

wherein $R^1$, $R^2$, $R^4$, $R^5$ and $R^8$ are each as defined above.

The reaction is usually carried out in the presence of a solvent. Any solvent may be employed insofar as it is inert to the reaction. Examples of the solvent are aromatic hydrocarbons (e.g. benzene, toluene), ethers (e.g. diethyl ether, tetrahydrofuran), halogenated hydrocarbons (e.g. carbon tetrachloride, chloroform, dichloromethane), aliphatic hydrocarbons (e.g. n-hexane, cyclohexane), amides (e.g. dimethylformamide), etc. These can be used either individually or in combination. This reaction may also be carried out in the absence of any solvent when the compound (IV) is liquid. In general, the reaction is adequately effected at a temperature between $-100°$ C. and $100°$ C.

The obtained compound (V) is then, if necessary, subjected to hydrolysis to produce a compound of the formula:

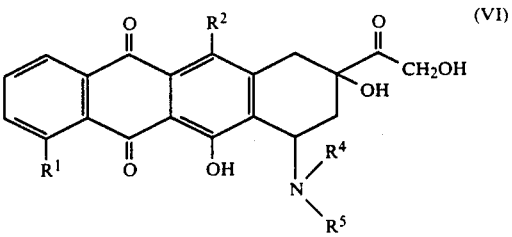

wherein $R^1$, $R^2$, $R^4$ and $R^5$ are each as defined above. Conventional and ordinary conditions for the hydrolysis under acidic or alkaline media may be applied to this reaction.

The compounds (V) and (VI) obtained as above may be converted into acid addition salts with inorganic or organic acids. Molar ratio of the acid to the compound (V) or (VI) in the said acid addition salts can be adjusted by varying an amount of the acid to provide, for example, a monoacidic salt or a diacidic salt. Any acid may be employed insofar as it can form a pharmaceutically acceptable salt, and examples of the acid are inorganic acids such as hydrochloric acid and hydrobromic acid, and organic acids such as acetic acid, malic acid, citric acid and tartaric acid, etc, etc.

The compound (I) of the invention is intended to cover the following four isomers with respect to the configurations for the asymmetric carbon atoms at the 7- and 9-positions.

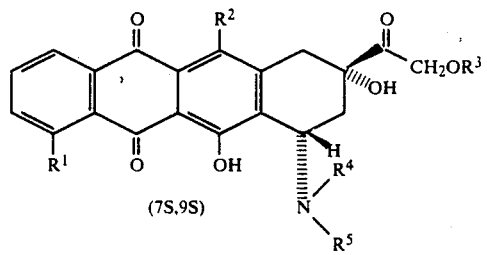

(7S,9S)

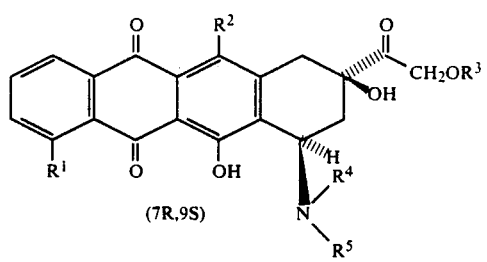

(7R,9S)

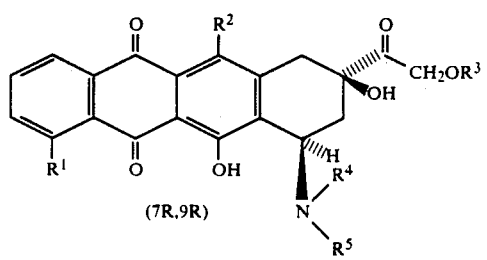

(7R,9R)

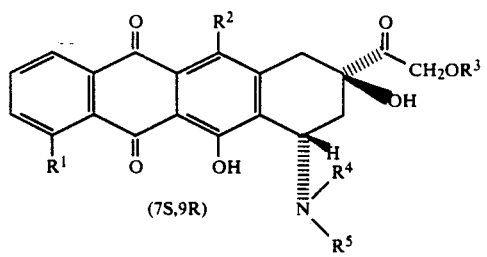

(7S,9R)

wherein $R^1$, $R^2$, $R^3$, $R^4$ and $R^5$ are each as defined above.

It is to be understood that all these isomers are included in the present invention, and the (7S,9S) isomer is the most preferable among them.

The compound (III) as the starting material in the above process can be prepared, for example, by the method illustrated below.

A compound of the formula:

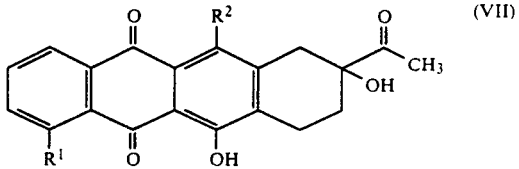

(VII)

wherein $R^1$ and $R^2$ are each as defined above, which is the known substance, is reacted with a halogenating agent to produce a compound of the formula:

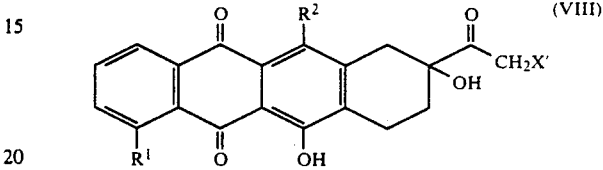

(VIII)

wherein $R^1$ and $R^2$ are each as defined above and X' is a halogen atom.

Examples of the halogenating agent include bromine, N-bromosuccinimide, N-chlorosuccinimide, pyrrolidone hydrotribromide, pyridine hydroperbromide, etc. A solvent such as dichloromethane, chloroform, carbon tetrachloride, tetrahydrofuran, diethyl ether, benzene, toluene or dimethylformamide may be used as the reaction medium. The reaction is usually carried out at a temperature between 0° and 100° C.

The obtained compound (VIII) is reacted, in a solvent, with a compound of the formula:

$$R^8COOM \qquad (IX)$$

wherein $R^8$ is a lower alkyl group and M is an alkali metal atom (e.g. lithium, sodium, potassium) or an alkaline earth metal atom (e.g. calcium, barium) to produce a compound of the formula:

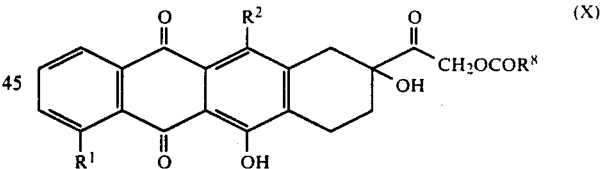

(X)

wherein $R^1$, $R^2$ and $R^8$ are each as defined above.

Examples of the solvent include diethyl ether, tetrahydrofuran, acetone, methylethylketone, dimethylformamide, benzene, toluene, etc. The reaction is usually carried out at a temperature of 0° to 100° C.

The obtained compound (X) is further reacted with a halogenating agent to give the compound (III). Examples of the halogenating agent are N-bromosuccinimide, N-chlorosuccinimide, etc. The reaction proceeds generally at or above room temperature and can be accelerated by warming. If necessary, a radical initiator such as azobisisobutyronitrile or benzoyl peroxide may be added to the reaction system. Alternatively, an irradiation by visible light may be applied. The reaction is usually carried out in an appropriate solvent. Any solvent may be employed insofar as it causes no adverse effect to the halogenation reaction. Examples of the solvent are halogenated hydrocarbons (e.g. carbon tetrachloride, chloroform, dichloromethane), aromatic hydrocarbons (e.g. benzene), ethers (e.g. diethyl ether, tetrahydrofuran, dioxane, diglyme), amides (e.g. dimethylformamide), aliphatic hydrocarbons (e.g. n-hexane, cyclohexane), acetic acid, water, etc. These can be used either individually or in combination.

The aminonaphthacenes (I) exhibit an extremely excellent anti-tumor activity. Though the presently used clinical anti-timor agents such as Adriamycin (ADR) and Daunomycin (DMC) have an excellent anti-tumor activity on one hand, they on the other hand show a strong adverse effect such as cardiotoxicity. In addition, these anthracycline antibiotics are difficult to be separated and purified from natural sources in the manufacturing process. Accordingly, many attempts have been made to produce novel analogues of ADR and DMC, especially those in which the sugar-moiety is changed by chemical modification or total synthesis. However, there has never been reported any analogue which has a non-sugar-substituent in place of the sugar-moiety and shows a significant anti-tumor activity. For instance, Journal of Medicinal Chemistry, Vol. 22, No. 8, pp. 922-926 discloses that the 7-O-$\beta$-alanine ester of Daunomycinone and the 7-O-$\beta$-aminoethyl ether of Daunomynicone exhibited only a lowest borderline effect on to P388 leukemia in animal experiments using mice.

The aminonaphthacenes (I) of the invention exhibit an excellent growth inhibition against P388 tumor cell (in vitro) as shown in the following table:

| Compound | Concentration ($\mu$/ml) | |
|---|---|---|
| | 1 | 0.1 |
| 9-Acetoxyacetyl-7-(2-dimethyl-aminoethyl)amino-6,9,11-trihydroxy-5,7,8,9,10,12-hexahydro-naphthacene-5,12-dione | 64.0 [68.3] | 66.4 [61.2] |
| 7(S)—(2-Dimethylaminoethyl)amino-9(S)—acetoxyacetyl-6,9,11-trihydroxy-5,7,8,9,10,12-hexahydro-naphthacene-5,12-dione | 100 (98.9) | 97.3 (98.5) |
| 7(S)—(2-Dimethylaminoethyl)amino-9(S)—hydroxyacetyl-6,9,11-trihydroxy-5,7,8,9,10,12-hexahydro-naphthacene-5,12-dione | 94.6 (94.1) | 90.1 (93.2) |
| 7(S)—(2-Dimethylaminoethyl)amino-9(S)—valeryloxyacetyl-6,9,11-trihydroxy-5,7,8,9,10,12-hexahydro-naphthacene-5,12-dione | 91.1 (90.2) | 90.4 (90.4) |
| 7(S)—(2-Dimethylaminoethyl)amino-9(S)—valeryloxyacetyl-4,6,9,11-tetrahydroxy-5,7,8,9,10,12-hexa-hydronaphthacene-5,12-dione | 93.2 (97.4) | 85.4 (96.4) |

Note:
The values in brackets [ ] are the inhibitory concentrations determined on DMC.
The values in parentheses ( ) are the inhibitory concentrations determined on ADR.

The aminonaphthacenes (I) also exhibit a significant survival effect onto mice carrying P388 tumor cells.

Accordingly, the aminonaphthacenes (I) are useful as anti-tumor agents. They can be administered parenterally, orally or locally to warm-blooded animals and human beings in the form of conventional pharmaceutical preparations. For instance, they can be administered in the form of conventional solid pharmaceutical preparations such as tablets, capsules, powders or granules, or in the form of conventional liquid pharmaceutical preparations such as suspensions, emulsions or solutions. The daily dosage may vary depending upon the administration route and is usually between 0.1 and 100 mg/kg.

The invention will now be further illustrated by means of the following Reference Examples and Examples, which are not, however, intended to limit the scope of the invention.

REFERENCE EXAMPLE 1

(1) Reaction of 9-acetyl-6,9,11-trihydroxy-5,7,8,9,10,12-hexahydronaphthacene-5,12-dione (352 mg) with pyrrolidone hydrotribromide (562 mg) was effected in tetrahydrofuran (50 ml) at room temperature for 40 hours. After removing insoluble materials by filtration, the filtrate was concentrated under reduced pressure to give 9-bromoacetyl-6,9,11-trihydroxy-5,7,8,9,10,12-hexahydronaphthacene-5,12-dione, which was used in the next step without purification.

(2) The entire amount of 9-bromoacetyl-6,9,11-trihydroxy-5,7,8,9,10,12-hexahydronaphthacene-5,12-dione obtained in (1) above was dissolved in acetone (30 ml). Sodium acetate (410 mg) was added to the solution, and the mixture was allowed to stand at room temperature for 10 hours. The solvent was removed under reduced pressure, and the residue was dissolved in dichloromethane. The solution obtained was washed with water, dried over sodium sulfate and concentrated under reduced pressure, followed by removal of the most part of the solvent to give orange crystals of 9-acetoxyacetyl-6,9,11-trihydroxy-5,7,9,9,10,12-hexahydronaphthacene-5,12-dione. M.P., 183°-186° C. This compound was filtered, and the filtrate was chromatographed over a silica gel column using a mixture of dichloromethane and methanol (9:1) to give additional crystals of the acetate compound.

(3) A mixture of 9-acetoxyacetyl-6,9,11-trihydroxy-5,7,8,9,10,12-hexahydronaphthacene-5,12-dione (3.74 g), chloroform (140 ml), carbon tetrachloride (300 ml) and water (280 ml) was treated with bromine (7.5 g) under reflux for 1 hour in the presence of azobisisobutyronitrile (340 mg) as a radical initiator. The reaction mixture was cooled to 10°-15° C. to precipitate reddich orange powders mainly consisting of 9-acetoxyacetyl-7-bromo-6,9,11-trihydroxy-5,7,8,9,10,12-hexahydronaphthacene-5,12-dione. After drying, the said powders were used as the materials for the next step without further treatment.

EXAMPLE 1

(1) To N,N-dimethyl ethylenediamine (10 ml) was added 9-acetoxyacetyl-7-bromo-6,9,11-trihydroxy-5,7,8,9,10,12-hexahydronaphthacene (500 mg) obtained in Reference Example 1-(3) under cooling with dry ice/acetone.

After the addition was completed, the reaction mixture was stirred in an ice bath for 1 hour. Then, the mixture was poured into ice water, adjusted to around pH 8.0 and extracted with dichloromethane. The extract was treated in the conventional manner and the obtained mixture of products was purified by silica gel chromatography using a mixture of dichloromethane and methanol (9:1) to give dark orange crystals of 9-acetoxyacetyl-7-$\beta$-N,N-dimethylaminoethylamino-6,9,11-trihydroxy-5,7,8,9,10,12-hexahydronaphthacene-5,12-dione. M.P., 134.5° C. (decomp.).

IR (Nujol) $\nu$cm$^{-1}$: 3300, 1750, 1740, 1630, 1590.

NMR (CDCl$_3$) $\delta$: 1.57-1.87 (m, 1H), 2.12-3.35 (m, 9H), 2.20 (s, 3H), 2.26 (s, 6H), 4.25 (bs, 1H), 5.27 (q, 1H), 7.56-7.88 (m, 2H), 8.00-8.32 (m, 2H).

MS (Field Desorption Mass Spectrometry) m/e: 497 (M+1)$^+$.

Dihydrochloride of the product had a melting point of 143°–151° C.

(2) To 20% aqueous hydrogen chloride was added 9-acetoxyacetyl-7-β-N,N-dimethylaminoethylamino-6,9,11-trihydroxy-5,7,8,9,10,12-hexahydronaphthacene-5,12-dione (300 mg) at −5°–0° C. and the resultant mixture was allowed to react at the same temperature for 2 hours. The mixture was then adjusted to around pH 8.0 and extracted with dichloromethane. The extract was treated in the conventional manner to give dark orange crystals of 7-β-N,N-dimethylaminoethylamino-9-hydroxyacetyl-6,9,11-trihydroxy-5,7,8,9,10,12-hexahydronaphthacene-5,12-dione. M.P., 213°–228° C.

IR (Nujol) $\nu cm^{-1}$: 3300, 1718, 1620, 1580.

NMR (CDCl$_3$) δ: 1.60–3.45 (m, 1H), 2.24 (s, 6H), 4.31 (bs, 1H), 4.75 (bs, 2H), 7.78 (m, 2H), 9.27 (m, 2H).

MS m/e: 455 (M+1)$^+$.

Dihydrochloride of the product had a melting point of 164°–174° C.

The same compound as above was obtained as by-product in the purification step by silica gel chromatography in Reference Example 1-(3).

REFERENCE EXAMPLE 2

(1) A mixture of 9-bromoacetyl-6,9,11-trihydroxy-5,7,8,9,10,12-hexahydronaphthacene-5,12-dione (1.00 g) obtained in Reference Example 1-(1), sodium valerate (1.44 g) and acetone (50 ml) was stirred under reflux for 5 hours, cooled to room temperature and concentrated under reduced pressure. The residue was triturated with an adequate quantity of ether, and solid substances were filtered to give reddish crystals of 9-valeryloxyacetyl-6,9,11-trihydroxy-5,7,8,9,10,12-hexahydronaphthacene-5,12-dione. M.P., 170°–172° C.

IR (Nujol) $\nu cm^{-1}$: 3400, 1775, 1770, 1620, 1585.

NMR (CDCl$_3$) δ: 0.83–3.15 (m, 16H), 5.12 (bs, 2H), 7.80 (m, 2H), 8.30 (m, 2H), 13.37 (bs, 2H).

(2) In the same manner as in Reference Example 1-(3), 9-valeryloxyacetyl-6,9,11-trihydroxy-5,7,8,9,10,12-hexahydronaphthacene-5,12-dione (700 mg) was brominated to give reddish orange powders mainly consisting of 7-bromo-9-valeryloxyacetyl-6,9,11-trihydroxy-5,7,8,9,10,12-hexahydronaphthacene-5,12-dione, which were used in the next step without purification.

EXAMPLE 2

In the same manner as in Example 1-(1), 7-bromo-9-valeryloxyacetyl-6,9,11-trihydroxy-5,7,8,9,10-12-hexahydronaphthacene-5,12-dione (870 mg) obtained in Reference Example 2-(2) was reacted with N,N-dimethylethylenediamine (10 ml). After the usual post-treatment was obtained dark orange crystals of 7-β-N,N-dimethylaminoethylamino-9-valeryloxyacetyl-6,9,11-trihydroxy-5,7,8,9,10,12-hexahydronaphthacene-5,12-dione. M.P., 128°–133° C.

IR (Nujol) $\nu cm^{-1}$: 3300, 1740, 1735, 1620, 1585.

NMR (CDCl$_3$) δ: 0.83–3.27 (m, 17H), 2.22 (s, 6H), 4.32 (bs, 1H), 5.26 (q, 2H), 7.80 (m, 2H), 8.30 (m, 2H).

MS m/e: 539 (M+1)$^+$.

REFERENCE EXAMPLE 3

(1) Reaction of 9-acetyl-6,9-dihydroxy-5,7,8,9,10,12-hexahydronaphthacene-5,12-dione (690 mg) with pyrrolidone hydrotribromide (1.15 g) was effected in tetrahydrofuran (70 ml) at room temperature for 40 hours. After removing insoluble matters by filtration, the solvent was distilled off under reduced pressure to give yellow crystals (785 mg, 92%) of 9-bromoacetyl-6,9-dihydroxy-5,7,8,9,10,12-hexahydronaphthacene-5,12-dione. M.P., 179°–180° C.

IR (Nujol) $\nu cm^{-1}$: 3520, 1720, 1670, 1630, 1580.

(2) To a solution of 9-bromoacetyl-6,9-dihydroxy-5,7,8,9,10,12-hexahydronaphthacene-5,12-dione (780 mg) in acetone (64 ml) was added sodium acetate (1.6 g) and the mixture was allowed to react at room temperature for 65 hours. After removing insoluble matters by filtration, the most part of the solvent was distilled off under reduced pressure and subjected to filtration to give yellow crystals (560 mg, 76%) of 9-acetoxyacetyl6,9-dihydroxy-5,7,8,9,10,12-hexahydronaphthacene-5,12-dione. M.P., 203°–206° C.

IR (Nujol) $\nu cm^{-1}$: 3970, 1735, 1700, 1665, 1625, 1580.

NMR (CDCl$_3$+DMSO-d$_6$) δ: 1.80–2.20 (m, 2H), 2.13 (s, 3H), 2.80–3.95 (m, 5H), 5.26 (s, 2H), 7.50 (s, 1H), 7.70–7.90 (m, 2H), 9.16–8.26 (m, 2H).

(3) A mixture of 9-acetoxyacetyl-6,9dihydroxy-5,7,8,9,10,12-hexahydronaphthacene-5,12-dione (515 mg), chloroform (75 ml), carbon tetrachloride (30 ml) and water (20 ml) was treated with bormine (418 mg) for 1 hour in the presence of azobisisobutyronitrile (107 mg) as a radical initiator. The reaction mixture were separated into two phases, of which the organic phase was washed with water (50 ml×3) and saturated aqueous sodium chloride solution (50 ml×3) and dried over sodium sulfate. The most part of the solvent was removed under reduced pressure to give yellowish brown crystals (400 mg, 65%) of 9-acetoxyacetyl-7-bromo-6,9-dihydroxy-5,7,8,9,10,12-hexanhydronaphthacene-5,12-dione. M.P., 206.5°–240° C.

IR (Nujol) $\nu cm^{-1}$: 3460, 1740, 1720, 1650, 1625, 1580.

EXAMPLE 3

To N,N-dimethyl ethylenediamine (6 ml) was added 9-acetoxyacetyl-7-bromo-6,9-dihydroxy-5,7,8,9,10,12-hexahydronaphthacene-5,12-dione (350 mg) under cooling with dry ice/acetone. After the addition was completed, the reaction mixture was stirred in an ice bath for 1 hour. Then, the reaction mixture was poured into ice water, adjusted to around pH 8.0 and extracted with dichloromethane. The extract was treated in the conventional manner and the obtained mixture of products was purified by silica gel chromatography using a mixture of dichloromethane and methanol (9:1) to give yellow crystals of 9-acetoxyacetyl-7-β-N,N-dimethylaminoethylamino-6,9-dihydroxy-5,7,8,9,10,12-hexahydronaphthacene-5,12-dione.

IR (Nujol) $\nu cm^{-1}$: 3500, 1740, 1720, 1670, 1630, 1580.

NMR (CDCl$_3$) δ: 1.65–1.90 (m, 1H), 2.15–3.46 (m, 9H), 2.20 (s, 3H), 2.30 (s, 6H), 4.35 (bs, 1H), 5.25 (q, 1H), 7.60 (s, 1H), 7.70–7.88 (m, 2H), 8.17–8.36 (m, 2H).

REFERENCE EXAMPLE 4

(1) Reaction of 9(R)-acetyl-6,9,11-trihydroxy-5,7,8,9,10,12-hexahydronaphthacene-5,12-dione ($[\alpha]_D^{20}=-87°$ (c=0.1, CHCl$_3$)) (11.5 g) with pyrrolidone hydrotribromide (18.19 g) was effected in tetrahydrofuran (1380 mg) at room temperature for 40 hours. After removing insoluble matters by filtration, the solvent was distilled off under reduced pressure to give 9(R)-bromoacetyl-6,9,11-trihydroxy-5,7,8,9,10,12-hexahydronaphthacene-5,12-dione, which was used in the next step without purification.

(2) The entire amount of 9(R)-bromoacetyl-6,9,11-trihydroxy-5,7,8,9,10,12-hexahydronaphthacene-5,12-dione obtained in (1) above was dissolved in acetone (1200 ml). Sodium acetate (9.25 g) was added thereto and the mixture was allowed to react at room temperature for 18 hours. After removing insoluble matters by filtration, the solvent was removed under reduced pressure. The residue was dissolved in dichloromethane. The resultant mixture was washed with water, dried over sodium sulfate and concentrated under reduced pressure. Ether (50 ml) was added to the residue. The mixture thus obtained was stirred at room temperature for 30 hours and precipitated crystals were filtered to give orange crystals of 9(R)-acetoxyacetyl-6,9,11-trihydroxy-5,7,8,9,10,12-hexahydronaphthacene-5,12-dione. M.P., 220°–222° C. $[\alpha]_D^{20} = -19.6°$ (c=0.1, CHCl$_3$).

(3) Treatment of 9(R)-acetoxyacetyl-6,9,11-trihydroxy-5,7,8,9,10,12-hexahydronaphthacene-5,12-dione (3.5 g) with bromine (3.41 g) was effected in a refluxing mixture of chloroform (875 ml) and carbon tetrachloride (1750 ml) with heating for 3 hours, while the reaction mixture was irradiated with 500 W lamp as radical reaction initiator in the presence of cyclohexene oxide (2.51 g) as a scavenger of the generated HBr. The solvent was removed under reduced pressure and ether (52.5 ml) was added to the residue. The resultant mixture was stirred at room temperature for 1.5 hours and precipitated crystals were filtered to give reddish orange powders of 7-bromo-9(S)-acetoxyacetyl-6,9,11-trihydroxy-5,7,8,9,10,12-hexahydronaphthacene-5,12-dione. M.P., 173°–175° C.

EXAMPLE 4

(1) To a solution of 7-bromo-9(S)-acetoxyacetyl-6,9,11-trihydroxy-5,7,8,9,10,12-hexahydronaphthacene-5,12-dione (2.5 g) obtained in Reference Example 4-(3) in dichloromethane (250 ml) was added a solution of N,N-dimethyl ethylenediamine (0.54 g) silylated with bistrimethylsilylacetamide (2.08 g) in dichloromethane (25 ml). After allowed to react for 1 hour, water (50 ml) was added to the mixture, which was then stirred for an additional 1 hour. The mixture was adjusted to pH 8.0. The organic layer was washed with water, dried over sodium sulfate and concentrated under reduced pressure. Dichloromethane (10 ml) and ether (20 ml) were added to the residue and precipitated crystals were filtered to give dark orange crystals of 7(S)-β-N,N-dimethylaminoethylamino-9(S)-acetoxyacetyl-6,9,11-trihydroxy-5,7,8,9,10,12-hexahydronaphthacene-5,12-dione. M.P., 128°–133° C. $[\alpha]_D^{20} = +175.8°$ (c=0.1, CHCl$_3$).

Dihydrochloride of the product had a melting point of 157°–160° C.

(2) To 20% aqueous hydrochloric acid (15 ml) was added 7(S)-β-N,N-dimethylaminoethylamino-9(S)-acetoxyacetyl-6,9,11-trihydroxy-5,7,8,9,10,12-hexahydronaphthacene-5,12-dione (100 mg) obtained in (1) above at −5°–0° C., and the resultant mixture was allowed to react at the same temperature for 4 hours. After adjusting to pH 8.0, the mixture was extracted with dichloromethane and post-treated in the usual manner to give dark orange crystals of 7(S)-β-N,N-dimethylaminoethylamino-9(S)-hydroxyacetyl-6,9,11-trihydroxy-5,7,8,9,10,12-hexahydronaphthacene-5,12-dione. M.P., 188°–192° C.

Dihydrochloride of the product had a melting point of 193°–198° C.

EXAMPLE 5

In the same manner as in Example 4-(1), 7-bromo-9(S)-acetoxyacetyl-6,9,11-trihydroxy-5,7,8,9,10,12-hexahydronaphthacene-5,12-dione (250 mg) obtained in Reference Example 4 was treated with N,N-dimethylaminopropylamine (63 mg) and the reaction product was post-treated to give dark orange crystals of 7(S)-β-N,N-dimethylaminopropylamino-9(S)-acetoxyacetyl-6,9,11-trihydroxy-5,7,8,9,10,12-hexahydronaphthacene-5,12-dione. M.P., 110°–112° C. $[\alpha]_D^{20} = +203.2°$ (c=0.1, CHCl$_3$).

NMR (CDCl$_3$) δ: 1.55–2.0 (m, 4H), 2.2 (s, 3H), 2.3 (s, 6H), 2.38–2.6 (m, 4H), 2.8–3.16 (m, 4H), 4.25 (bs, 1H, ν½ 7.5 Hz), 5.2 (q, 2H, J=12 Hz), 7.7–7.9 (m, 2H), 8.1–9.35 (m, 2H).

MS m/e: 511 (M+1)$^+$.

Dihydrochloride of the product had a melting point of 150°–154° C.

EXAMPLE 6

In the same manner as in Example 4-(1), 7-bromo-9(S)-acetoxyacetyl-6,9,11-trihydroxy-5,7,8,9,10,12-hexahydronaphthacene-5,12-dione (200 mg) obtained in Reference Example 4 was treated with ethanolamine (30 mg) and the reaction product was post-treated to give dark reddish brown crystals of 7(S)-β-hydroxyethylamino-9(S)-acetoxyacetyl-6,9,11-trihydroxy-5,7,8,9,10,12-hexahydronaphthacene-5,12-dione. M.P., 100°–103° C. $[\alpha]_D^{20} = +166.2°$ (c=0.1, CHCl$_3$).

NMR (CDCl$_3$) δ: 1.55–1.85 (m, 1H), 2.2 (s, 3H), 1.95–2.55 (m, 1H), 2.85–0.2 (m, 4H), 3.55–4.1 (m, 2H), 4.23 (bs, 1H, ν½ 7.5 Hz), 5.25 (q, 2H, J=12 Hz), 7.6–7.85 (m, 2H), 7.9–8.15 (m, 2H), 7.9–8.15 (m, 2H).

MS m/e: 470 (M+1)$^+$.

Hydrochloride of the product had a melting point of 174°–178° C.

REFERENCE EXAMPLE 5

(1) A mixture of 9(R)-bromoacetyl-6,9,11-trihydroxy-5,7,8,9,10,12-hexahydronaphthacene-5,12-dione (1.00 g) obtained in Reference Example 4-(1), sodium octate (4.8 g) and acetone (50 ml) was stirred under reflux for 3 hours, cooled to room temperature and concentrated under reduced pressure. The residue was triturated with addition of ether (15 ml). Solid substances were filtered to give orange crystals of 9(R)-octyloxyacetyl-6,9,11-trihydroxy-5,7,8,9,10,12-hexahydronaphthacene-5,12-dione. M.P., 144°–148° C.

IR (Nujol) νcm$^{-1}$: 3650–3100, 1730, 1620, 1590.

NMR (CDCl$_3$) δ: 0.85 (s, 3H), 1.3 (bs, 7H), 1.5–2.3 (m, 5H), 2.42 (t, 2H), 2.97 (bs, 4H), 5.25 (s, 2H), 7.64–7.9 (m, 2H), 8.05–8.34 (m, 2H).

MS m/e: 494 (M)$^+$.

(2) In the same manner as in Reference Example 4-(3), 9(R)-octyloxyacetyl-6,9,11-trihydroxy-5,7,8,9,10,12-hexahydronaphthacene-5,12-dione (954 mg) was brominated to give reddish orange powders of 7-bromo-9(S)-octyloxyacetyl-6,9,11-trihydroxy-5,7,8,9,10,12-hexahydronaphthacene-5,12-dione. M.P., 134°–136.5° C. MS m/e: 574 (M+1)$^+$.

EXAMPLE 7

In the same manner as in Example 4-(1), 7-bromo-9(S)-octyloxyacetyl-6,9,11-trihydroxy-5,7,8,9,10,12-hexahydronaphthacene-5,12-dione (1.09 g) obtained in Reference Example 5 was treated with N,N-dimethyl ethylenediamine and the reaction product was post-treated to give dark orange crystals of 7(S)-β-N,N-dimethylaminoethylamino-9(S)-octyloxyacetyl-6,9,11-trihydroxy-5,7,8,9,10,12-hexahydronaphthacene-5,12- dione. M.P. 125°–128° C. $[\alpha]_D^{20} = +200°$ (c=0.02, CHCl$_3$).

IR (Nujol) $v$cm$^{-1}$: 3600–3200, 1740, 1720, 1620, 1590.

NMR (CDCl$_3$) δ: 0.92–3.20 (m, 23H), 2.35 (s, 6H), 4.23 (bs, 1H), 5.26 (q, 2H), 7.6–7.85 (m, 2H), 8.05–8.3 (m, 2H).

MS m/e: 581 (M+1)$^+$.

REFERENCE EXAMPLE 6

(1) A mixture of 9(R)-bromoacetyl-6,9,11-trihydroxy-5,7,8,9,10,12-hexahydronaphthacene-5,12-dione (1.00 g) obtained in Reference Example 4-(1), sodium valerate (1.44 g) and acetone (50 ml) was stirred under reflux for 2 hours. After removing insoluble matters by filtration, the reaction mixture was concentrated under reduced pressure. The residue was treated with ether (15 ml) and precipitated crystals were collected by filtration to give orange crystals of 9(R)-valeryloxyacetyl-6,9,11-trihydroxy-5,7,8,9,10,12-hexahydronaphthacene-5,12-dione. M.P., 149°–152° C.

IR (Nujol) $v$cm$^{-1}$: 1730, 1620, 1585.

NMR (CDCl$_3$) δ: 1.93 (t, J=6 Hz, 3H), 1.16–2.30 (m, 6H), 2.32–2.63 (m, 2H), 2.93 (bs, 4H), 5.20 (s, 2H), 7.60–7.87 (m, 2H), 8.00–8.26 (m, 2H).

(2) In the same manner as in Reference Example 4-(3), 9(R)-valeryloxyacetyl-6,9,11-trihydroxy-5,7,8,9,10,12-hexahydronaphthacene-5,12-dione (600 mg) was brominated to give reddish orange powders of 7-bromo-9(S)-valeryloxyacetyl-6,9,11-trihydroxy-5,7,8,9,10,12-hexahydronaphthacene-5,12-dione.

EXAMPLE 8

In the same manner as in Example 4-(1), 7-bromo-9(S)-valeryloxyacetyl-6,9,11-trihydroxy-5,7,8,9,10,12-hexahydronaphthacene-5,12-dione (the whole quantity) obtained in Reference Example 6 was treated with N,N-dimethyl ethylenediamine and the reaction product was post-treated to give dark orange crystals of 7(S)-β-N,N-dimethylaminoethylamino-9(S)-valeryloxyacetyl-6,9,11-trihydroxy-5,7,8,9,10,12-hexahydronaphthacene-5,12-dione. M.P. 126°–133° C. $[\alpha]_D^{20} = +165°$ (c=0.1, CHCl$_3$).

IR (Nujol) $v$cm$^{-1}$: 1720, 1620, 1590.

NMR (CDCl$_3$) δ: 1.96 (t, J=7 Hz, 3H), 1.20–1.90 (m, 6H), 2.28 (s, 6H), 2.32–3.30 (m, 8H), 4.20 (bs, 1H), 5.25 (q, J=8 Hz, 2H), 7.60–7.83 (m, 2H), 7.93–8.23 (m, 2H).

MS m/e: 539 (M+1)$^+$.

REFERENCE EXAMPLE 7

(1) A mixture of 7-deoxydaunomycinone (350 mg, prepared from daunomycin hydrochloride by the process described in Journal of Organic Chemistry, 42 (23), 3657 (1977)), anhydrous aluminum chloride (1.1 g) and dichloromethane (36.3 ml) was stirred under reflux for 4 hours. The reaction mixture was poured into a 5% aqueous oxalic acid solution (160 ml). After addition of dichloromethane (1500 ml), the resultant mixture was stirred under reflux for 1 hour and cooled. Two phases in the mixture were separated and the organic layer was dried over sodium sulfate and concentrated. The residue was treated with ether (30 ml) and the precipitated crystals were collected by filtration to give reddish orange crystals of 7-deoxycarminomycinone. M.P., 247°–249° C.

IR (Nujol) $v$cm$^{-1}$: 3480, 1700, 1620, 1600.

NMR (CDCl$_3$) δ: 1.7–2.0 (m, 2H), 2.2 (s, 3H), 2.7–3.0 (m, 4H), 7.15–7.4 (m, 1H), 7.5–7.95 (m, 2H), 11.8–12.3 (m, 1H), 12.3–12.7 (m, 1H), 13.3–13.6 (m, 1H).

MS m/e: 368 (M)$^+$.

(2) In the same manner as in Reference Example 4-(1), 7-deoxycarminomycinone (333 mg) was brominated to give reddish brown crystals of 9(R)-bromoacetyl-4,6,9,11-tetrahydroxy-5,7,8,9,10,12-hexahydronaphthacene-5,12-dione, which was used in the next step without purification.

(3) The entire amount of 9(R)-bromoacetyl-4,6,9,11-tetrahydroxy-5,7,8,9,10,12-hexahydronaphthacene-5,12-dione was dissolved in acetone (110 ml). Potassium acetate (270 mg) was added to the above solution and the mixture was allowed to react at room temperature for 2 hours, followed by addition of water (100 ml). The precipitated crystals were collected by filtration to give reddish orange crystals of 9(R)-acetoxyacetyl-4,6,9,11-tetrahydroxy-5,7,8,9,10,12-hexahydronaphthacene-5,12-dione. M.P. 215°–217° C.

IR (Nujol) $v$cm$^{-1}$: 3600–3300, 1740, 1730, 1600.

NMR (CDCl$_3$) δ: 2.1 (s, 3H), 2.6–2.9 (m, 4H), 1.7–2.0 (m, 2H), 5.2 (s, 2H), 7.1–7.35 (m, 1H), 7.5–7.9 (m, 2H), 11.75–12.0 (m, 1H), 12.3–12.55 (m, 1H,

MS m/e: 426 (M)$^+$.

(4) In the same manner as in Reference Example 4-(3), 9(R)-acetoxyacetyl-4,6,9,11-tetrahydroxy-5,7,8,9,10,12-hexahydronaphthacene-5,12-dione (374 mg) was brominated to give reddish orange crystals of 7-bromo-9(S)-acetoxyacetyl-4,6,9,11-tetrahydroxy-5,7,8,9,10,12-hexahydronaphthacene-5,12-dione, which were used in the next step without purification.

EXAMPLE 9

In the same manner as in Example 4-(1), the whole quantity of 7-bromo-9(S)-acetoxyacetyl-4,6,9,11-tetrahydroxy-5,7,8,9,10,12-hexahydronaphthacene-5,12-dione obtained in Reference Example 7-(4) was treated with N,N-dimethyl ethylenediamine (93 mg) and the reaction product was post-treated to give dark orange crystals of 7(S)-β-N,N-dimethylaminoethylamino-9(S)-acetoxyacetyl-4,6,9,11-tetrahydroxy-5,7,8,9,10,12-hexahydronaphthacene-5,12-dione. M.P. 134°–136° C.

IR (Nujol) $v$cm$^{-1}$: 3600–3200, 1740, 1730, 1600.

NMR (CDCl$_3$) δ: 2.15 (s, 3H), 2.47 (s, 6H), 1.5–3.4 (m, 8H), 4.17 (bs, 1H), 5.2 (q, J=8 Hz, 2H), 7.0–7.15 (m, 1H), 7.43–7.85 (m, 2H).

MS m/e: 513 (M+1)$^+$.

Dihydrochloride of the product had a melting point of 166°–170° C.

REFERENCE EXAMPLE 8

(1) In the same manner as in Reference Example 1-(1), 7-deoxycarminomycinone (170 mg) prepared in the same manner as in Reference Example 7-(1) was brominated to produce 9(R)-bromoacetyl-4,6,9,11-tetrahydroxy-5,7,8,9,10,12-hexahydronaphthacene-5,12-dione. The whole quantity of this compound was dissolved in acetone. Sodium valerate (320 mg) was added to this solution and the resultant mixture was heated under reflux for 2 hours. After removing insoluble matters by filtration, the reaction mixture was concentrated under reduced pressure. The residue was treated with water (100 ml) and precipitated crystals were collected by filtration to give reddish orange crystals of 9(R)-valeryloxyacetyl-4,6,9,11-tetrahydroxy-5,7,8,9,10,12-hexahydronaphthacene-5,12-dione. M.P., 225°–227° C.

IR (Nujol) $v$cm$^{-1}$: 3450, 1720, 1600, 1590.

MS m/e: 468 (M)$^+$.

(2) In the same manner as in Reference Example 1-(3), 9(R)-valeryloxyacetyl-4,6,9,11-tetrahydroxy- 5,7,8,9,10,12-hexahydronaphthacene-5,12-dione (180 mg) was brominated to give reddish orange crystals of 7-bromo-9(S)-valeryloxyacetyl-4,6,9,11-tetrahydroxy-5,7,8,9,10,12-hexahydronaphthacene-5,12-dione, which were used in the next step without purification.

EXAMPLE 10

In the same manner as in Example 1-(1), the entire amount of 7-bromo-9(S)-valeryloxyacetyl-4,6,9,11-tetrahydroxy-5,7,8,9,10,12-hexahydronaphthacene-5,12-dione obtained in Reference Example 8 was treated with N,N-dimethyl ethylenediamine (40 mg) and the reaction product was post-treated to give dark orange crystals of 7(S)-β-N,N-dimethylaminoethylamino-9(S)-valeryloxyacetyl-4,6,9,11-tetrahydroxy-5,7,8,9,10,12-hexahydronaphthacene-5,12-dione. MS m/e: 554 $(M+1)^+$.

Dihydrochloride of the product had a melting point of 152°–153° C.

REFERENCE EXAMPLE 9

(1) In the same manner as in Reference Example 1-(1), 7-deoxydaunominomycinone (348 mg) was brominated to give 14-bromo-7-deoxydaunomycinone (MS m/e: 461 $(M)^+$) which was used in the next step without purification.

(2) In the same manner as in Reference Example 8-(1), the entire amount of 14-bromo-7-deoxydaunomycinone obtained in (1) above was treated with sodium valerate to give reddish orange crystals of 14-valeryloxy-7-deoxydaunomycinone. M.P. 226°–229° C.

IR (Nujol) $\nu cm^{-1}$: 3460, 1740, 1720, 1600, 1580.
MS m/e: 483 $(M+1)^+$.

(3) In the same manner as in Reference Example 1-(3), 14-valeryloxy-7-deoxydaunomycinone (356 mg) was brominated to give reddish orange crystals of 7-bromo-14-valeryloxydaunomycinone, which were used in the next step without purification.

EXAMPLE 11

In the same manner as in Example 1-(1), the whole quantity of 7-bromo-14-valeryloxydaunomycinone obtained in Reference Example 9 was treated with N,N-dimethyl ethylenediamine (78 mg) and the reaction product was post-treated to give dark orange crystals of 7(S)-β-N,N-dimethylaminoethylamino-9(S)-valeryloxyacetyl-4-methoxy-6,9,11-trihydroxy5,7,8,9,10,12-hexahydronaphthacene-5,12-dione. MS m/e: 569 $(M+1)^+$.

Dihydrochloride of the product had a melting point of 150°–152° C.

What is claimed is:

1. An aminonaphthacene derivative of the formula:

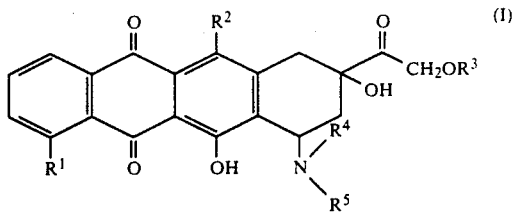

wherein $R^1$ is a hydrogen atom, a hydroxyl group or a lower alkoxy group, $R^2$ is a hydrogen atom or a hydroxyl group, $R^3$ is a hydrogen atom or a lower alkanoyl group and $R^4$ and $R^5$ are, same or different, each a hydrogen atom, a lower alkyl group, a lower hydroxyalkyl group or a group of the formula:

wherein A is an alkylene group which may have one or more lower alkyl substituent(s) and $R^6$ and $R^7$ are, same or different, each a hydrogen atom, a lower alkyl group, a lower hydroxyalkyl group or a lower aminoalkyl group, and an acid addition salt thereof.

2. The aminonaphthacene derivative according to claim 1, wherein $R^4$ is

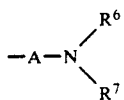

wherein $R^6$ and $R^7$ are each lower alkyl and A is as defined in claim 1 and $R^5$ is hydrogen.

3. The aminonaphthacene derivative according to claim 2, wherein $R^4$ is dimethylaminoethyl.

4. The aminonaphthacene derivative according to claim 3, wherein $R^2$ is hydroxyl.

* * * * *